United States Patent
Mortensen et al.

[11] Patent Number: 5,881,718
[45] Date of Patent: Mar. 16, 1999

[54] VALVE

[75] Inventors: Preben Korntved Mortensen, Greve; Stig Waldorff, Hörholm, both of Denmark

[73] Assignee: Astra Aktiebolag, Sodertalje, Sweden

[21] Appl. No.: 501,133
[22] PCT Filed: Mar. 24, 1995
[86] PCT No.: PCT/SE95/00313
    § 371 Date: Aug. 15, 1995
    § 102(e) Date: Aug. 15, 1995
[87] PCT Pub. No.: WO95/27525
    PCT Pub. Date: Oct. 19, 1995

[30] Foreign Application Priority Data
    Apr. 11, 1994 [SE] Sweden .................... 9401220

[51] Int. Cl.⁶ .................................................. A61M 16/00
[52] U.S. Cl. ................................ 128/203.11; 128/205.24
[58] Field of Search ........................ 128/205.24, 207.12, 128/205.13, 202.28, 202.29, 203.12, 204.26

[56] References Cited

U.S. PATENT DOCUMENTS

| | | | |
|---|---|---|---|
| 4,520,811 | 6/1985 | White et al. | 128/203.11 |
| 4,521,038 | 6/1985 | Fesny | 128/205.13 |
| 4,622,964 | 11/1986 | Flynn | 128/205.24 |
| 4,811,730 | 5/1989 | Milano | 128/203.11 |
| 4,886,057 | 12/1989 | Nave | 128/203.11 |
| 4,998,530 | 3/1991 | Mieharel | 128/203.11 |
| 5,012,803 | 5/1991 | Foley et al. | 128/200.23 |
| 5,109,840 | 5/1992 | Daleiden | 128/205.24 |
| 5,357,951 | 10/1994 | Natnes | 128/205.13 |
| 5,456,249 | 10/1995 | Nirle | 128/205.24 |
| 5,501,214 | 3/1996 | Sabo | 128/205.24 |

FOREIGN PATENT DOCUMENTS

| | | | |
|---|---|---|---|
| 384050 A1 | 8/1990 | European Pat. Off. | |
| 1356338 | 2/1964 | France . | |
| 7214463-7 | 8/1976 | Sweden . | |
| 8700925-4 | 9/1988 | Sweden . | |
| 1034759 | 7/1966 | United Kingdom . | |
| 2162070 | 1/1986 | United Kingdom | 128/205.24 |

Primary Examiner—John G. Weiss
Assistant Examiner—V. Scrivastava
Attorney, Agent, or Firm—Fish & Richardson P.C.

[57] ABSTRACT

Valve intended to be used in particular in inhalation devices having a body, such as a spacer, the valve having a housing comprising an first part which is adapted to be mounted on an outlet opening of the body of the inhalation device, a second part on to which a mouthpiece or a face mask can be mounted, said first and second parts being provided with a first bore defining an inhalation channel, a first membrane provided in the inhalation channel and a second membrane, wherein the second part is provided with a second bore, said second bore defining the exhalation channel, the two channels being provided separated from one another and placed adjacent each other.

21 Claims, 2 Drawing Sheets

VALVE

FIELD OF THE INVENTION

The present invention relates to a valve intended to be used in particular in inhalation devices having a container, a so called spacer. The valve has a housing comprising a first part which is adapted to be mounted on an outlet opening of the body of the inhalation device, a second part on which a mouthpiece or a face mask can be mounted, said first and second parts being provided with a bore defining an inhalation channel, a first membrane provided in the inhalation channel and a second membrane.

In particular the invention relates to a spacer device to be attached to a metered dose inhaler, a so called aerosol device for use in the treatment of infants and young children.

When dealing with bronchial diseases, such as bronchitis and asthma, among young children and infants, it is a problem to make them inhale the medical substances. When asthma for example makes its debut among young children such as infants from 6 months up to 4.5–5 years it is especially difficult to make the infant inhale the prescribed medical substances correctly in the proper way. It is also a want among the parents that the used devices should be as easy to use as possible.

BACKGROUND OF INVENTION

Persons suffering from bronchial diseases such as asthma, have a limited lung capacity and the force of the breath is limited. This is even more apparent when the patient is a small child or an infant.

It is therefore of utmost importance that a device which is intended to be used by a small child or an infant is constructed in a manner which reduces the inhalation force and capacity needed to inhale the required amount of substance. It is also important that the tidal volume is small and that the dead space i.e. the space defined between the spacer outlet/valve inlet and the valve outlet/mouth piece/face mask is as small as possible in order to avoid or at least minimize the rebreathing of the exhalation air, e.g. $CO_2$.

It is therefore important that the valve mounted in the spacer at its outlet opening is constructed in a manner giving the smallest possible resistance and the minimal dead space and that it works in the required manner even when subjected to weak inhalation forces.

PRIOR ART

Several different devices have been developed to be used for inhalation treatment in small children and infants. Most of them are stationary devices which have to be placed in hospitals and which are expensive and complicated. They are often acting with pumps providing an airflow for the infant to inhale which means that no force at all is needed from the infant. These devices have shown to be very good. A stationary device shows a lot of drawbacks for the user and in the case of small children and infants for the parents as well. As the inhalation capacity of an infant is limited, the administration will be time consuming, which of course also is inconvenient.

Devices known in the prior art are provided with one way valves to prevent exhalation air from entering into the spacer body. These valves require a certain inhalation flow to open and a small child or infant is not capable to generate the required inhalation flow to open the valve in the proper way.

In U.S. Pat. No. 5,012,803 a spacer is described having a thin diaphragm of plastic or elastomeric material provided in the inhalation channel acting as an inhalation valve and an exhalation valve located in a specially designed face mask. No special efforts have been taken in order to minimize the dead space within the valve and this device is not designed to be used by small children or infants.

In GB 2 230 456 a spacer for small children is described. It is provided with an inhalation valve and an exhalation valve. The inhalation valve comprises a disk which is biased into a closed position in which it bears against an annular seat by means of a spring.

Other types of inhalation valves could be used such as for example a cone-diaphragm valve. The inhalation valve should be constructed in such a manner that it opens as soon as the pressure on the outlet side is less than the pressure on the inlet side and the difference should be low. The exhalation valve comprises a disk trapped within a cylindrical chamber.

The valves known in the prior art have several drawbacks. They are constructed with several parts which are complicated to mount and expensive to produce. In the valve described in the above mentioned GB 2 230 456 the inhalation valve and the exhalation valve are both mounted within the same chamber. No efforts have been made in this construction to minimize the dead space. On the contrary, due to the construction with a separate exhalation valve provided within the same chamber as the inhalation valve the dead space is increased. Moreover, the inhalation valve comprises a centrally positioned disc which during inhalation moves axially. The particles in the inhalation flow will be obstructed by the valve disc and will lead to a reduction of the substance to be inhaled as well as to a soiling of the valve. Furthermore, the location of the exhalation valve within the inhalation chamber will cause humidity from the exhalation air to stay within the inhalation chamber and due to this the particles contained in the inhalation air flow will stick to the walls of the chamber. The reduction of the substance will have to be compensated for, which could be done by giving a greater dose and letting the child inhale for a longer time. This is of course not desirable when dealing with small children and infants. Further, in the known devices the valves are complicated to take apart and clean.

THE INVENTION

It is therefore an object of the present invention to provide a valve which aims to reduce the draw backs of the known devices and is simple and cheap to produce.

This solution is achieved by the characterising features of claim 1, the second part of the valve housing is provided with a second bore, said second bore defining the exhalation channel, the two channels being provided separated from one another and placed adjacent each other.

Further preferred embodiments are described in the dependent claims 2 to 9.

It is also an object of the present invention to provide a use of a valve as described in claim 10, as well as a method of assembling a valve as described in claim 11.

BRIEF DESCRIPTION OF THE DRAWINGS

The valve according to the present invention will now be described by way of example with reference to the appended drawings, wherein

FIGS. 4a and 4b show two different side views of the first membrane mounted in the inhalation channel of the valve, and FIG. 5 shows a side view of the second membrane mounted in the exhalation channel of the valve.

DETAILED DESCRIPTION OF THE DRAWINGS

Figure 1:
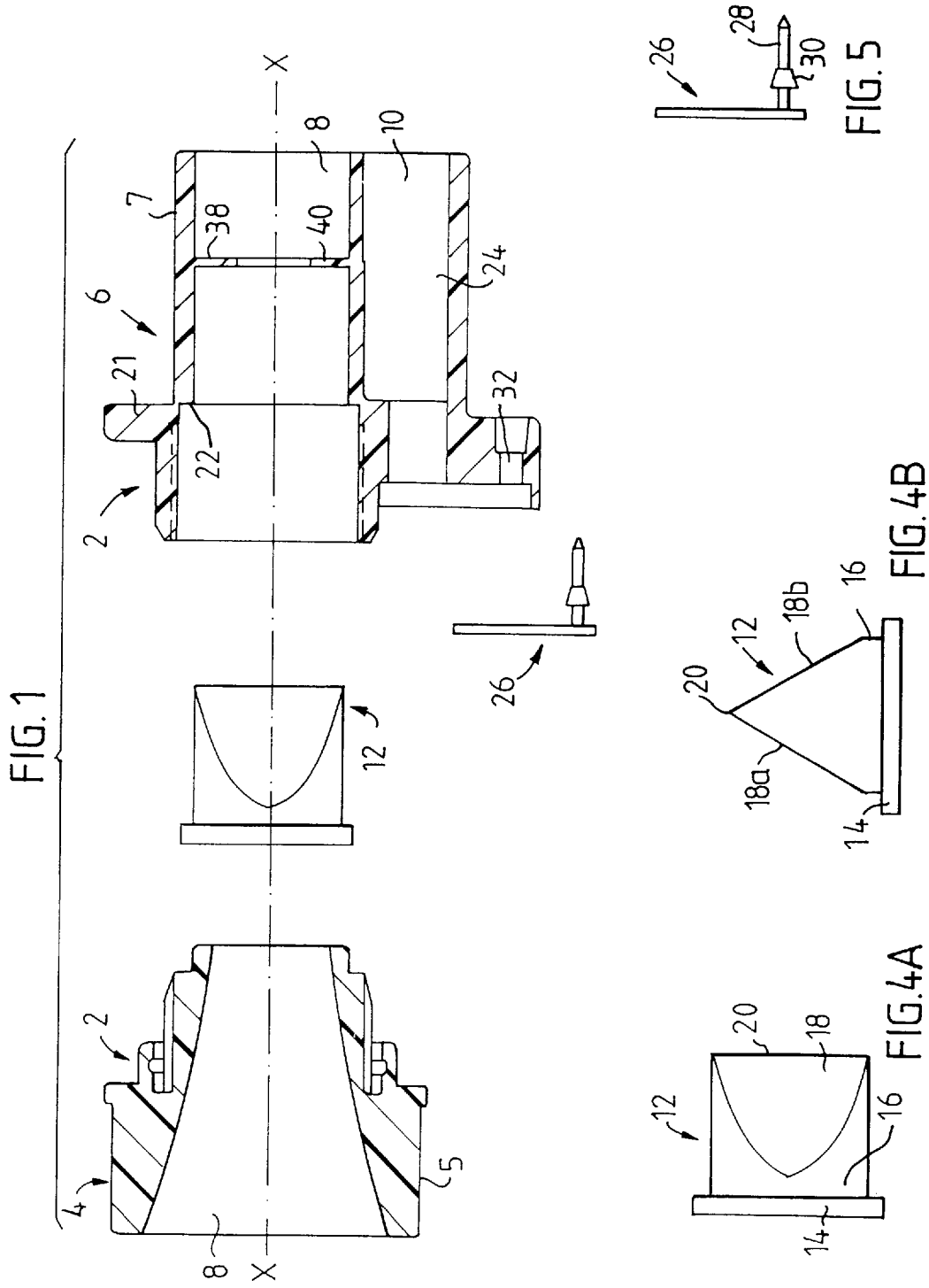
FIG. 1 shows an exploded view of a valve according to a preferred embodiment of the description.

The valve is now described in relation to a preferred embodiment of the valve according to the invention.

The valve according to the invention has a housing 2 consisting of two parts, a first part 4 and a second part 6 which are intended to be joined together. The first part 4 is adapted to be fitted to the outlet end of an inhalation device having a body, e.g. a so called spacer. The spacer is preferably constructed to be used by small children the spacer preferably having a volume between 150 to 500 ml more preferably about 250 ml, but could of course have any desired volume and form. The adaptor part 5 of the first part 4 is adapted to be fitted to a spacer and is preferably constructed to be fully inserted into the corresponding part of the spacer. Furthermore, the end part 7 of the second part 6 is adapted to be fitted to a mouthpiece or a face mask and is preferably constructed to be fully inserted into the corresponding part of the face mask or mouthpiece. By constructing the end parts to be fully inserted into the corresponding parts of the spacer and the facemask or mouthpiece a contribution to the aim to minimize the deadspace within the device is obtained. The other end part of the second part 6 is intended to be joined with the first part and has a greater cross sectional area than this first part 4.

The first and the second parts are provided with a bore which forms the inhalation channel 8 when the two parts are joined together. In the preferred embodiment the inhalation channel 8 is provided along the central axis X—X of the first part 4 but is provided along an axis which is parallel with and displaced in relation to the central axis of the second part 6. Due to this displacement of the exhalation channel from the inhalation channel in the second part a part 10 is formed which protrudes beyond the extension of the first part 4 when the two parts are joined together.

In the part of the inhalation channel which is positioned in the second part 6 a first membrane 12 is provided. This first membrane 12 constitutes the inhalation valve and is formed to be opened by the inhalation airflow through the inhalation channel 8 during inhalation. As can be seen in FIGS. 4a and 4b the membrane 12 is formed with an edge 14 at one end of the main body 16. The main body 16 has the form of a cylinder which is cut by two planes 18a and 18b. The two planes 18a, 18b form an angle of substantially about 60° with each other. In the angle between the two planes a line is formed in which an opening 20 is provided as indicated in FIGS. 4a and 4b. The edge 14 is intended to be placed within a recess 22 provided in the wall of the inhalation channel 8 in the second part 6. When the first and second parts are joined together the edge of the membrane will be kept within the recess 22 by the end edge of the first part 4.

It is important for the function of the valve that the membrane 12 is made of a soft and flexible material. In particular the walls of the membrane must be flexible which means that they have to be as thin as possible as the opening in the membrane must open even to small air pressures. The membrane 12 in the inhalation valve is constructed to open at an air pressure just above 0 Pa or mmHg.

In the preferred embodiment the membrane is made of silicone, ethylene-propylene terpolymer (ethylene-propylene-diene monomer or EPDM), or chloroprene but any other suitable material having similar characteristics, e.g. being soft and flexible, can be used.

In a preferred construction of the valve a thin perforated wall 38 is provided in the inhalation channel of the second part 6. This perforated wall 38 is provided with a plurality of holes 40 for the air flow and as a security wall which prevents the membrane 12 from being damaged if a foreign object is inserted into the inhalation channel. It is also a security wall for the user to ensure that the membrane 12 cannot get into the mouth and lungs of the user if it is released from its position. The perforated wall could be formed as a net or grid.

The function of the membrane will now be described in order to explain the importance of the choice of material and wall thickness in order to reduce the resistance during inhalation, this being one of the main objects of the invention. When the user inhales air flows through the inhalation channel 8 and through the membrane 12 as indicated by arrow A in FIG. 2. Due to the air flow the surfaces defined by the two planes 18a and 18b are separated whereby the opening 20 is opened and air can flow to the mouth piece or face mask fitted at the outlet opening of the valve. The thickness of the walls of the valve is preferably 0.15–0.2 mm for the materials in the preferred embodiment but if another material is used the thickness of the walls might be different for an optimal function of the valve.

Figure 2:
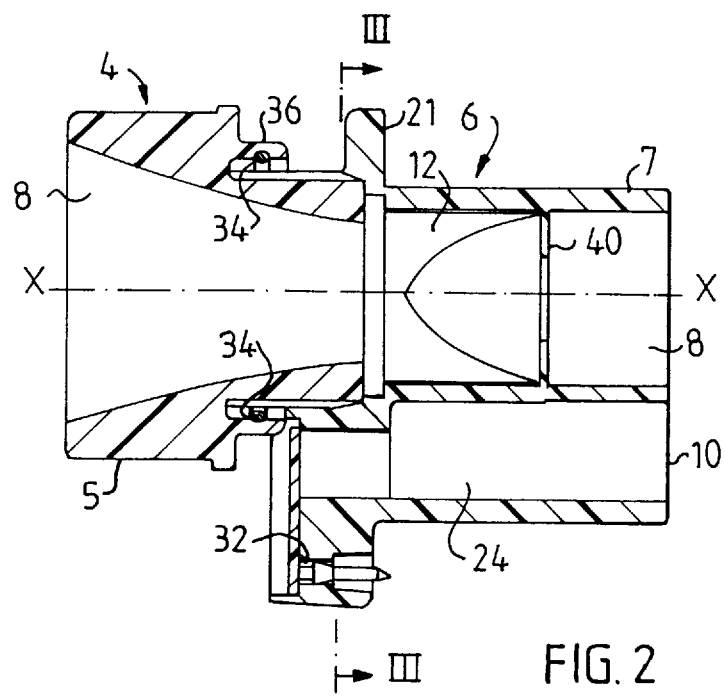
FIG. 2 shows the valve in the assembled position.
Figure 3:
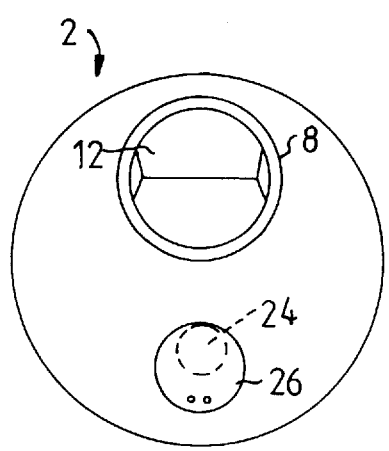
FIG. 3 shows a sectional view taken along the lines III—III in FIG. 2.

The second part 6 is provided with a further bore as can be seen in FIGS. 1, 2 and 3. This further bore is provided adjacent the inhalation channel 8 and in the part of the second part which protrudes beyond the extension of the first part 4. The second bore functions as the exhalation channel 24 and extends from the end part 7 of the second part 6 to the ambient air. A second membrane 26 is provided in the exhalation channel 24 and constitutes the exhalation valve, as can be seen in FIG. 5. The second membrane 26 is preferably substantially planar and circular and is provided with at least one, preferably two protruding retaining elements 28 provided adjacent each other and close to the periphery of the membrane. The exhalation valve in the preferred embodiment is constructed to open at an air pressure of about 30–40 Pa (40,8–54,4 mmHg). Arrow B in FIG. 2 indicates the air flow during exhalation.

In the preferred embodiment the retaining elements 28 extend substantially perpendicular to the plane of the membrane and are provided with a thickening 30 at their ends as can be seen in FIG. 5. The thickening 30 is intended to form retaining means for the membrane 26. The membrane 26, the retaining elements 28 and the thickenings 30 are preferably made of the same material. Said material must be soft and flexible and in order to simplify the manufacture of the valve according to the invention the first and second membranes are made of the same material.

Adjacent the exhalation channel 24 the second part is provided with at least one, preferably two, bores 32. The bores 32 have two parts, one part having a diameter corresponding to the diameter of the retaining elements 28 and one part having a diameter corresponding to the diameter of the thickenings 30.

The retaining elements 28 with their thickenings 30 are intended to be used for the mounting of the second membrane as follows. When the second membrane 26 is to be mounted in the exhalation channel 24 the retaining elements 28 with the thickenings are inserted into the bores 32 in such manner that the thickenings 30 extend beyond the bores. The thickenings will in this manner prevent the membrane 26 from falling off.

When joining the different parts of the valve together the first 12 and second 26 membranes are first placed in their respective position. The first membrane 12 is placed in the recess 22 in the second part 6 and the second membrane 26 is mounted as described above. The first and second part 4, 6 are thereafter joined together in any suitable manner. In the preferred embodiment these two parts are joined together by a snap-fitting. The second part 6 is provided with a collar 36 and the first part 4 is provided with a ridge 34. When the parts are joined the collar 36 of part 6 will snap in behind the ridge 34 of part 4 and the two parts will be securely joined together.

It is also possible to join the two parts by press-fitting during the actual manufacture of the valve. In this case one part is provided with an end part formed to be inserted into the corresponding end part of the second part. The two parts could also be screwed together by mutual engagement in screw threads arranged in the respective parts of the first and second part or by gluing or welding.

It is however important that no edges or recesses are formed within the inhalation or exhalation channels when the two parts are joined together on which substance particles, humidity and dust could stick during the use of the valve. This also facilitates a cleaning of the valve which could simply be performed by letting water or any other suitable cleaning fluid flow through the two channels of the valve.

In a preferred embodiment the two parts of the valve are produced in a plastic material which can be injection moulded. A preferred material is polysulfone.

MODIFICATIONS OF THE INVENTION

The valve according to the invention could of course be modified within the scope of the appended claims.

Thus the membranes in the inhalation and the exhalation valve could have other forms and be constructed differently. In the preferred embodiment the membrane in the inhalation valve is formed with two inclined planes 18*a* and 18*b* and an opening provided in the line along which these two planes meet each other, see FIG. 4*b*. The membrane could also be constructed with three planes inclined towards each other and a central opening provided at the point where the planes meet each other. This construction corresponds to the construction of a biological heart valve.

Furthermore, the exhalation channel, and the membrane provided in the exhalation channel could be semilunar and provided adjacent and around the inhalation channel. This construction would give a larger exhalation valve and channel and at the same time reduce the size of the valve housing.

We claim:

1. A valve assembly for an inhalation device, comprising:
    a housing comprising a first part having an inhalation bore extending therethrough and a second part having an inhalation bore and an exhalation bore extending therethrough, wherein the first and second parts are operatively coupled such that the inhalation bores form a continuous inhalation channel and the exhalation bore forms an exhalation channel adjacent and separate to the inhalation channel;
    a first valve disposed in the inhalation channel, the first valve being biased to a closed position and opened by an inhalation force; and
    a second valve disposed in the exhalation channel, the second valve being biased to a closed position and opened by an exhalation force;
    said inhalation and exhalation bores being arranged such that on inhalation by a patient air passes through only the inhalation channel and on exhalation by the patient air passes through only the exhalation channel.

2. The valve assembly according to claim 1, wherein the first part comprises first and second ends between which the inhalation bore extends, the first and second ends being adapted for coupling to an inhalation device and the second part, respectively.

3. The valve assembly according to claim 2, wherein the first end of the first part is constructed for insertion into a corresponding part of the inhalation device so that a dead space within the valve assembly is minimized.

4. The valve assembly according to claim 1, wherein the second part comprises first and second ends between which the inhalation bore and the exhalation bore extend, the first and second ends being adapted for coupling to a patient interface device and the first part, respectively.

5. The valve assembly according to claim 4, wherein the first end of the second part is constructed for insertion into a patient interface device so that a dead space within the valve assembly is minimized.

6. The valve assembly according to claim 1, wherein the first valve is secured within the inhalation channel by the coupling of the first and second parts.

7. The valve assembly according to claim 1, further comprising a perforated security wall disposed within the inhalation channel downstream of the first valve.

8. The valve assembly according to claim 4 or 5, wherein a patient interface device is either of a mouthpiece or a face mask.

9. The valve assembly according to claim 1, wherein the second valve comprises a planar membrane and at least one retaining element extending from the membrane for coupling the second valve to the exhalation channel so that the membrane is moveable between a first seated position when the second valve is closed and a second displaced position, the membrane being biased to the seated position and displaced by an exhalation force.

10. The valve assembly according to claim 9 or 7, wherein each retaining element comprises a shaft having a raised portion for insertion into a hole having sections of first and second dimension, the raised portion being operatively engaged behind the section of the hole having a smaller dimension.

11. The valve assembly according to claim 1, wherein the first and second parts are formed of polysulfone.

12. The valve assembly according to any one of claims 1 to 3, wherein the inhalation device is a spacer.

13. The valve assembly, according to claim 1, wherein the first valve comprises first and second wall members which enclose an angle of about 60° and meet at a line, the line forming an opening which is biased to a closed position and opened by an inhalation force.

14. The valve assembly according to claim 1, wherein the first valve comprises first, second and third wall members which are inclined towards each other and meet at a point, the point forming an opening which is biased to a closed position and opened by an inhalation force.

15. The valve assembly according to claims 13 or 14, wherein the first valve is formed from one of silicone, ethylene-propylene-diene monomer, or chloroprene.

16. The valve assembly of any one of claims 15, 13, or 14, wherein the wall members have a thickness of from 0.15 to 0.20 mm.

17. The valve assembly according to claim 9, wherein the membrane is circular.

18. The valve assembly according to claim 9 or 17, wherein at least one retaining element is located adjacent to the periphery of the membrane.

19. The valve assembly according to claim 1, wherein the second valve is disposed at the second end of the second part.

20. A spacer incorporating the valve assembly according to any one of claims 1–5.

21. A spacer incorporating the valve assembly according to any one of claims 1–5, further comprising a dispersion chamber having a volume of from 150 to 500 ml.

* * * * *